United States Patent [19]
Van Vlasselaer

[11] Patent Number: 5,648,223
[45] Date of Patent: *Jul. 15, 1997

[54] METHODS FOR ENRICHING BREAST TUMOR CELLS

[75] Inventor: Peter Van Vlasselaer, Sunnyvale, Calif.

[73] Assignee: Activated Cell Therapy, Inc., Mountain View, Calif.

[*] Notice: The term of this patent shall not extend beyond the expiration date of Pat. No. 5,474,687.

[21] Appl. No.: 299,465

[22] Filed: Aug. 31, 1994

[51] Int. Cl.$^6$ .......................... G01N 33/574; B01L 11/00
[52] U.S. Cl. .......................... 435/7.23; 210/781; 210/782; 435/2; 435/7.21; 435/7.24; 435/803; 436/514; 436/518; 436/527; 436/824; 422/72; 422/101; 422/102
[58] Field of Search .................................. 210/781, 782; 435/2, 7.21, 7.23, 7.24, 803; 436/514, 518, 527, 824; 422/72, 101, 102

[56] References Cited

U.S. PATENT DOCUMENTS

| | | | |
|---|---|---|---|
| 3,441,205 | 4/1969 | Young, Jr. . | |
| 3,513,976 | 5/1970 | James . | |
| 3,706,305 | 12/1972 | Berger et al. | 128/762 |
| 3,706,306 | 12/1972 | Berger et al. | 128/762 |
| 3,750,645 | 8/1973 | Bennett et al. | 128/760 |
| 3,849,072 | 11/1974 | Ayres | 210/789 |
| 3,862,303 | 1/1975 | Anderson | 436/531 |
| 3,937,211 | 2/1976 | Merten | 128/765 |
| 3,957,654 | 5/1976 | Ayres | 210/516 |
| 3,957,741 | 5/1976 | Rembaum et al. | 526/312 |
| 3,965,889 | 6/1976 | Sachs | 128/764 |
| 3,985,122 | 10/1976 | Topham | 128/765 |
| 4,001,122 | 1/1977 | Griffin | 210/516 |
| 4,020,831 | 5/1977 | Adler | 128/765 |
| 4,022,576 | 5/1977 | Parker | 436/177 |
| 4,035,316 | 7/1977 | Yen et al. | 521/65 |

(List continued on next page.)

FOREIGN PATENT DOCUMENTS

| | | |
|---|---|---|
| 198462A3 | 10/1986 | European Pat. Off. . |
| 0595641A2 | 10/1993 | European Pat. Off. . |
| 2115032 | 3/1971 | Germany . |
| WO91/07660 | 5/1991 | WIPO . |
| WO93/08268 | 4/1993 | WIPO . |
| WO93/08269 | 4/1993 | WIPO . |

OTHER PUBLICATIONS

Blanchard et al., "Infiltration of Interleukin-2-inducible Killer Cells in Ascitic Fluid and Pleural Effusions of Advanced Cancer Patients," *Cancer Research*, vol. 48, pp. 6321-6327, (1988).

Wallach et al., "Affinity Density Perturbation: A New Fractionation Principle and Its Illustration in a Membrane Separation," *FEBS Letters*, vol. 21, No. 1, pp. 29-33, (1972).

"The CD System," Dako, Inc., (1990).

(List continued on next page.)

*Primary Examiner*—Lora M. Green
*Assistant Examiner*—Susan C. Wolski
*Attorney, Agent, or Firm*—Carol A. Stratford; Peter J. Dehlinger

[57] ABSTRACT

The present invention relates to methods of enriching breast tumor cells from a patient's body fluids. In particular, it relates to the use of a cell-trap centrifugation tube containing a specific density gradient solution adjusted to a specific density to enrich for breast tumor cells from a cell mixture. The tube allows the desired cell population to be collected by decantation after centrifugation to minimize cell loss and maximize efficiency. In addition, the method can be further simplified by density-adjusted cell sorting which uses cell type-specific binding agents such as antibodies and lectins linked to carrier particles to impart a different density to the non-tumor or tumor cell populations allowing the breast tumor cells to be separated from the non-tumor cells in a more convenient manner. The rapid breast tumor cell enrichment method described herein has a wide range of applications, including but not limited to, detection of tumor cells by molecular and immunochemical means, and purging of tumor cells from an autologous bone marrow cell preparation prior to re-infusion.

18 Claims, 9 Drawing Sheets

U.S. PATENT DOCUMENTS

| | | | |
|---|---|---|---|
| 4,040,959 | 8/1977 | Berman et al. | 210/782 |
| 4,055,501 | 10/1977 | Cornell | 210/516 |
| 4,066,414 | 1/1978 | Selby | 422/102 |
| 4,105,598 | 8/1978 | Yen et al. | 521/53 |
| 4,112,924 | 9/1978 | Ferrara et al. | 128/764 |
| 4,134,512 | 1/1979 | Nugent | 215/247 |
| 4,147,628 | 4/1979 | Bennett et al. | 210/789 |
| 4,152,270 | 5/1979 | Cornell | 210/516 |
| 4,181,700 | 1/1980 | Chervenka | 422/101 |
| 4,203,840 | 5/1980 | Stoeppler | 210/787 |
| 4,213,456 | 7/1980 | Bottger | 604/226 |
| 4,256,120 | 3/1981 | Finley | 128/764 |
| 4,378,812 | 4/1983 | Sarstedt | 128/765 |
| 4,443,345 | 4/1984 | Wells | 210/782 |
| 4,459,997 | 7/1984 | Sarstedt | 128/764 |
| 4,510,244 | 4/1985 | Parks et al. | 435/172.2 |
| 4,511,349 | 4/1985 | Nielsen et al. | 494/16 |
| 4,511,662 | 4/1985 | Baran et al. | 436/513 |
| 4,533,468 | 8/1985 | Ensor et al. | 209/172 |
| 4,562,844 | 1/1986 | Carpenter et al. | 128/675 |
| 4,569,764 | 2/1986 | Satchell | 210/511 |
| 4,610,846 | 9/1986 | Martin | 422/101 |
| 4,707,276 | 11/1987 | Dodge et al. | 210/789 |
| 4,710,472 | 12/1987 | Saur et al. | 435/308.1 |
| 4,777,145 | 10/1988 | Luotola et al. | 436/526 |
| 4,824,560 | 4/1989 | Alspector | 209/208 |
| 4,828,716 | 5/1989 | McEwen et al. | 210/740 |
| 4,844,818 | 7/1989 | Smith | 210/789 |
| 4,886,071 | 12/1989 | Mehl et al. | 128/760 |
| 4,917,801 | 4/1990 | Luderer et al. | 210/516 |
| 4,927,749 | 5/1990 | Dorn | 435/2 |
| 4,927,750 | 5/1990 | Dorn | 435/2 |
| 4,954,264 | 9/1990 | Smith | 210/782 |
| 4,957,638 | 9/1990 | Smith | 210/782 |
| 4,983,369 | 1/1991 | Barder et al. | 423/338 |
| 5,030,341 | 7/1991 | McEwen et al. | 210/94 |
| 5,030,559 | 7/1991 | Nicolson et al. | 435/7.23 |
| 5,039,401 | 8/1991 | Columbus et al. | 210/177 |
| 5,045,201 | 9/1991 | Dubois et al. | 210/502.1 |
| 5,053,134 | 10/1991 | Luderer et al. | 210/516 |
| 5,132,232 | 7/1992 | Parker | 436/177 |
| 5,236,604 | 8/1993 | Fiehler | 210/782 |
| 5,248,480 | 9/1993 | Greenfield et al. | 422/68.1 |
| 5,260,186 | 11/1993 | Cercek et al. | 435/2 |
| 5,269,927 | 12/1993 | Fiehler | 210/516 |
| 5,271,852 | 12/1993 | Luoma, II | 210/789 |
| 5,279,936 | 1/1994 | Vorpahl | 435/6 |
| 5,308,506 | 5/1994 | McEwen | 210/745 |
| 5,314,074 | 5/1994 | Inbar | 209/208 |
| 5,474,687 | 12/1995 | Van Vlasselaer | 210/782 |

OTHER PUBLICATIONS

Dicke et al., 1968, "The Selective Elimination of Immunologically Competent Cells From Bone Marrow and Lymphatic Cell Mixtures," *Transplantation* 6(4):562–570.

Dicke et al., 1970, "Avoidance of Acute Secondary Disease by Purification of Hemopoietic Stem Cells with Density Gradient Centrifugation," *Exp. Hematol.* 20:126–130.

Dicke et al., 1971, "Allogeneic Bone Marrow Transplantation After Elimination of Immunocompetent Cells by Means of Density Gradient Centrifugation," *Transplantation Proceedings* 3(1):666–668.

Dicke et al., 1973, "The Use of Stem Cell Concentrates As Bone Marrow Grafts in Man," *Transplantation Proceedings* 5(1):909–912.

Korbling et al., 1977, "Procurement of Human Blood Stem Cells by Continuous–Flow Centrifugation—Further Comment," *Blood* 50:753–754.

Korbling et al., 1977, "In–Vitro and In–Vivo Properties of Canine Blood Mononuclear Leukocytes Separated by Discontinuous Albumin Density Gradient Centrifugation," *Biomedicine* 26:275–283.

Herzenberg et al., 1979, "Fetal Cells in the Blood of Pregnant Women: Detection and Enrichment by Fluorescence–Activated Cell Sorting" *Proc. Natl. Aca. Sci. USA* 76: 1453–5.

Osborne et al., 1980 "The Value of Estrogen and Progesterone Receptors in the Treatment of Breast Cancer" *Cancer* 46(12):2884–8.

Westley et al., 1980 "An Estrogen–Induced Protein Secreted By Human–Breast Cancer–Cells In Culture" *European Journal of Cell Biology* 22(1):397.

Gerdes et al., 1983 "Production of a Mouse Monoclonal Antibody Reactive with a Human Nuclear" *Current Biotech Abs.*

Kufe et al., 1984, "Differential Reactivity of a Novel Monoclonal Antibody (DF3) with Human Malignant Versus Benign Breast Tumors" *Hybridoma* 3(3):223–32.

Bray et al., 1987 "Serum Levels and Biochemical Characteristics of Cancer–Associated Antigen CA–549, a Circulating Breast Cancer Marker " *Cancer Res.* 47(22):5853–60.

Shpall et al., 1991, "Immunomagnetic purging of breast cancer from bone marrow for autologous transplantation," *Bone Marrow Transplantation* 7:145–151.

Lebkowski et al., 1992, "Rapid Isolation Of Human CD34 Hematopoietic Stem Cells—Purging of Human Tumor Cells," *Transplantation* 53(5):1011–1019.

Olofsson et al., 1983, "Separation of Human Bone Marrow in Density Gradients of Polyvinylpyrrolia Coated Silica Gel (Percoll)," *Second J. Pharmatol.* 24:254–262.

Osborne et al., 1980, "The Value of Estrogen and Progesterone Receptorsin the Treatment of Breast Cancer" *Cancer* 46(12):2884–8.

Westley et al., 1980, "An Estrogen–Induced Protein Secreted By Human–Breast Cancer Cells in Culture" *European Journal of Cell Biology* 22(1):397.

Gerdes et al., 1983 "Production of a Mouse Monoclonal Antibody Reactive with a Human Nuclear" *Current Biotech Abs.*

Ellis et al., 1984, "The Use of Discontinuous Percoll Gradients to Separate Populations of Cells from Human Bone Marrow and Peripheral Blood," *J. of Immunological Methods* 66;9–16.

Kufe et al., 1984, "Differential Reactivity of a Novel Monoclonal Antibody (DF3) with Human Malignant Versus Benign Breast Tumors" *Hybridoma* 3(3):223–32.

Lasky et al., 1985, "Size and Density Characterization of Human Committed and Multipotent Hematopoietic Progenitors" *Exp. Hematol.* 13:680–4.

Martin et al., 1986, "Purification of Haemopoietic Progenitor Cells From Patients with Chronic Granulocytic Leukaemia Using Percoll Density Gradients and Elutriation" *Brit. J. Haematol.* 63:187–98.

Bray et al., 1987 "Serum Levels and Biochemical Characteristics of Cancer–Associated Antigen CA–549, a Circulating Breast Cancer Marker" *Cancer Res* 47(22):5853–60.

Bianchi et al., 1990, "Isolation of fetal DNA from nucleated erythrocytes in maternal blood," *Proc Natl. Acad. Sci. USA* 87:3279–3283.

Price et al., 1991, "Prenatal diagnosis with fetal cells isolated from maternal blood by multiparameter flow cytometry," *Am. J. Obstet. Gynecol.* 165(6, part 1):1731–1737.

Shpall et al., 1991, "Immunomagnetic purgin of breast cancer fom bone marrow for autologous transplantation," *Bone Marrow Transplantation* 7:145–151.

Yoshioka et al., 1991, "Immobilization of ultra-thin layer of monoclonal antibody on glass surface," *J. of Chromolography* 566:361–368.

Durrant et al., 1992 "A Rapid Method for Separating Tumour Infiltrating Cells and Tumour Cells from Colorectal Tumours" *J. Immunol. Meth.* 147:57–64.

Elias et al., 1992, Session 12:Plenary Session, "Prenatal diagnosis of aneuploidy using fetal cells isolated form maternal blood" *Am. J. Hum. Genet,* 51:A4, Excerpt 5.

Ganshirt–Ahlert et al., 1992, Session 34:Prenatal and Perinatal Genetics II, and Molecular Applications in Clinical Genetics III, "Noninvasive prenatal diagnosis," *Am. J. Hum. Genet.* 51:A48 Excerpt 182.

Ganshirt–Ahlert et al., 1992, "Magnetic cell sorting and the transferrin receptor as potential means of prenatal diagnosis from maternal blood," *Am. J. Obstet. Gynecol.* 166(5):1350–1355.

Hall et al., 1992 "Prenatal and Perinatal Genetics, Isolation Purification of CD34+ Fetal Cells From Maternal Blood," *Am. J. Hum. Genet.* 51:A267, Excerpt 1013.

Harrison et al., 1992, Prenatal and Perinatal Genetics, "Use of fluorescence in site hybridization to detect confined placental mosaicism in trisomic conceptions," *Am. J. Hum. Genet.* 51:A257, Excerpt 1014.

Holzgreve et al., 1992, "Fetal Cells in the Maternal Circulation," *J. Reprod. Med.* 37(5) 410–418.

Ikuta et al., 1992, "Lymphocyte Development From Stem Cells", *Ann. Rev. Immunol.* 10:759–83.

Julien et al., 1992, Session 34:Prenatal and Perinatal Genetics II, and Molecular Applications in Clinical Genetics III, "Fetal cells in maternal blood," *Am. J. Hum. Genet.* 51:A48, Excerpt 181.

Lebkowski et al., 1992, "Rapid Isolation of Human CD34 Hematopoietic Stem Cell Purging of Human Tumor Cells", *Transplantation* 53(5):1011–1019.

Russo et al., 1992, *The Use of Resealed Erythrocytes as Carrier's and Bioreactors,* Published by Magnani & DeLoach, Plenum Press, New York, pp. 101–107.

Pope et al., 1993, "New Applications of Silane Coupling Agents for Covalently Binding Antibodies to Glass and Cellulose Solid Supports," *Bioconjugate Chem.* 4:166:171.

Schmitz et al., 1993, "Optimizing follicular dendritic cell isolation by discontinuous gradient centrifugation and use of the magnetic cell sorter (MACS)," *J. of Immunological Methods* 139:189–196.

Simpson et al., 1993, "Isolating Fetal Cells From Maternal Blood, Advances in Prenatal Diagnosis Through Molecular Technology," *Journal of American Medical Association (JAMA)* 270(19):2357–2361.

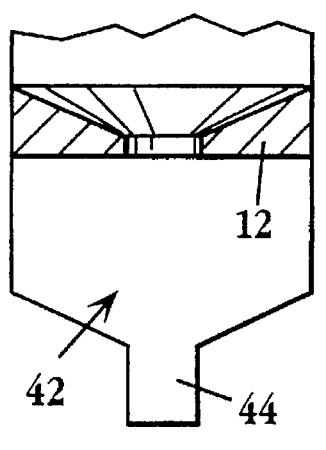 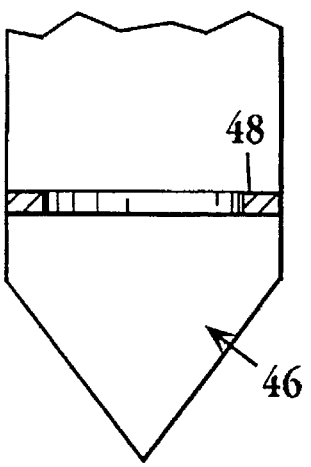 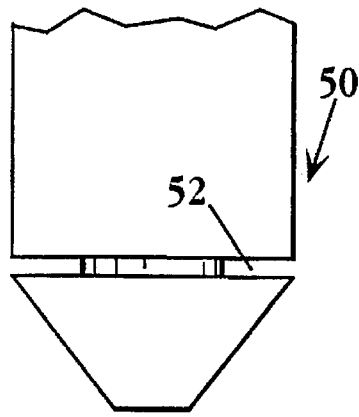
Fig. 5A  Fig. 5B  Fig. 5C
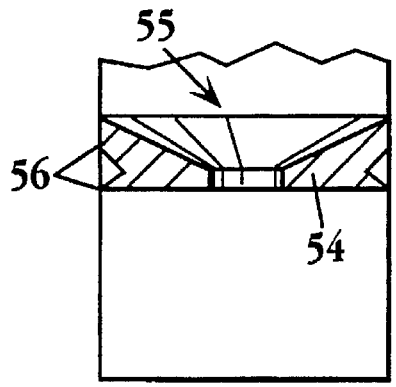 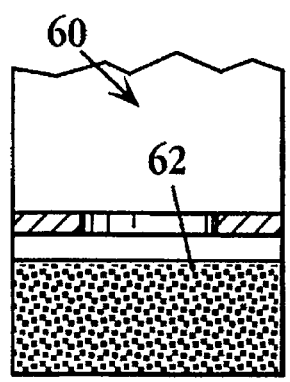 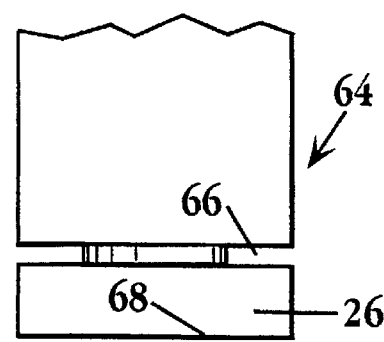
Fig. 5D  Fig. 5E  Fig. 5F
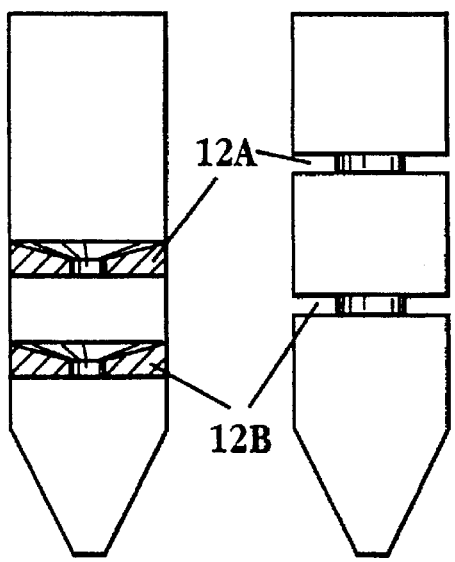
Fig. 6A  Fig. 6B

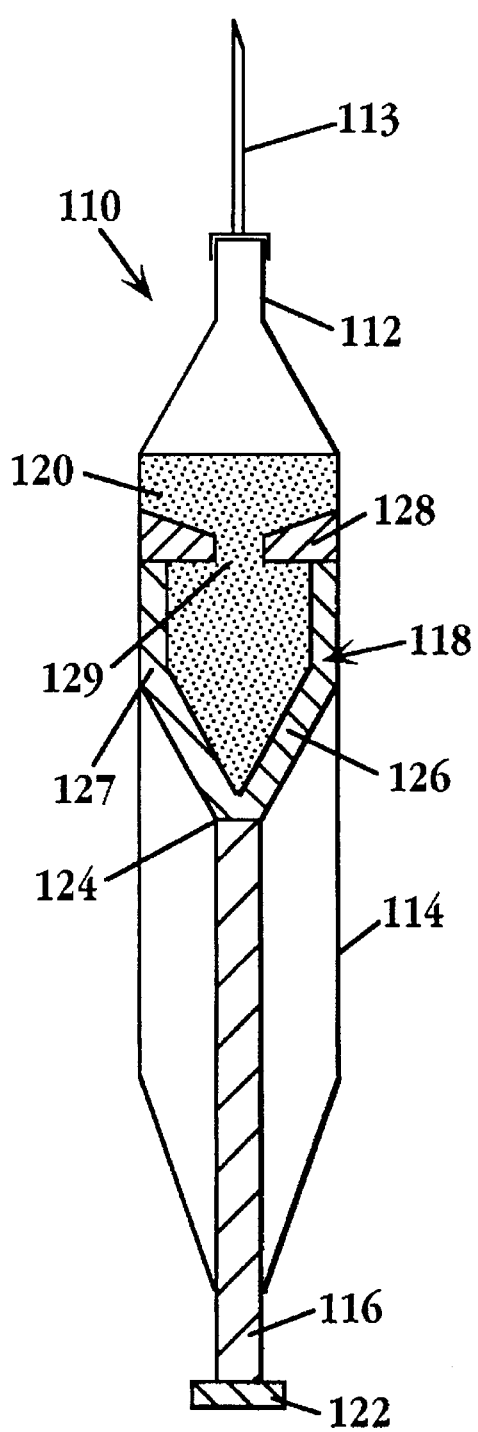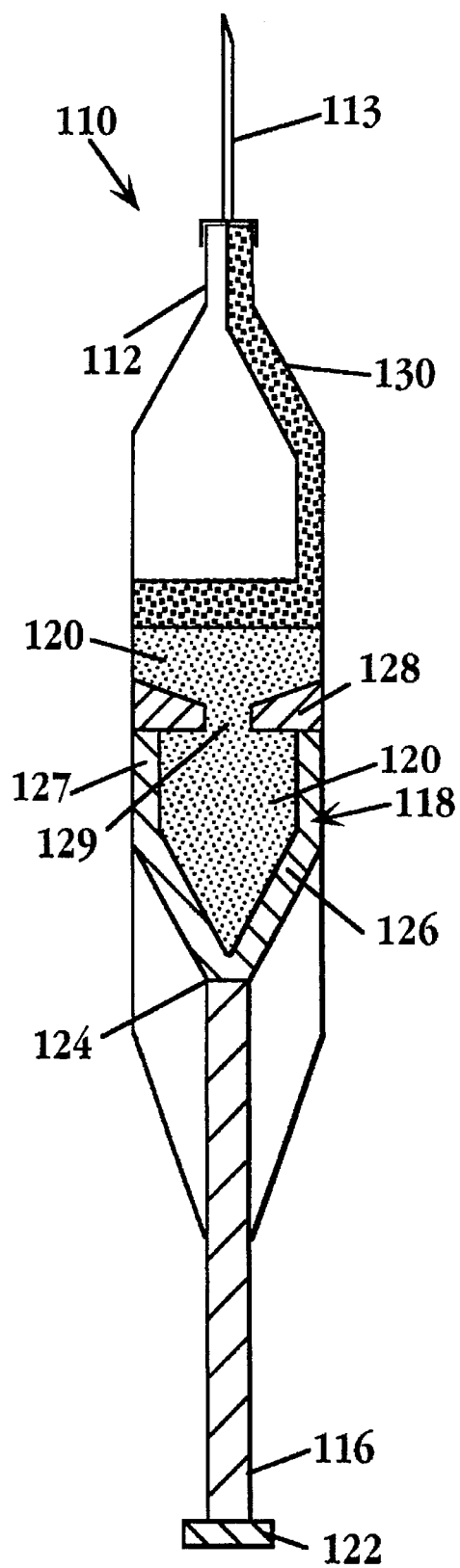
Fig. 7
Fig. 8

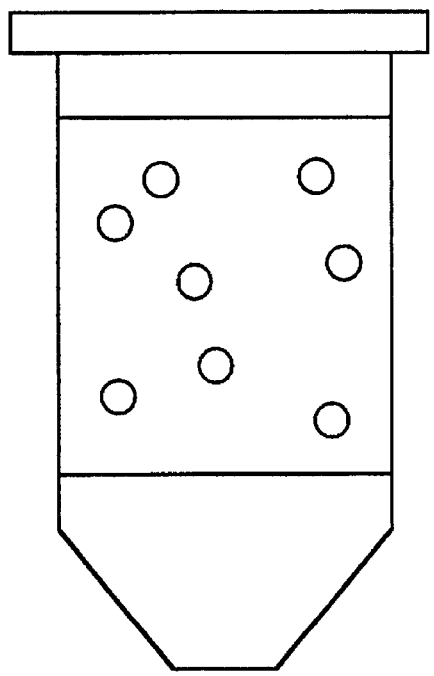
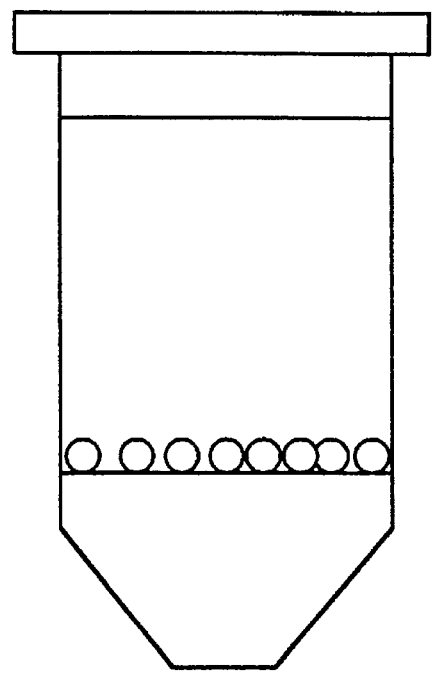
Fig. 11A        Fig. 11B
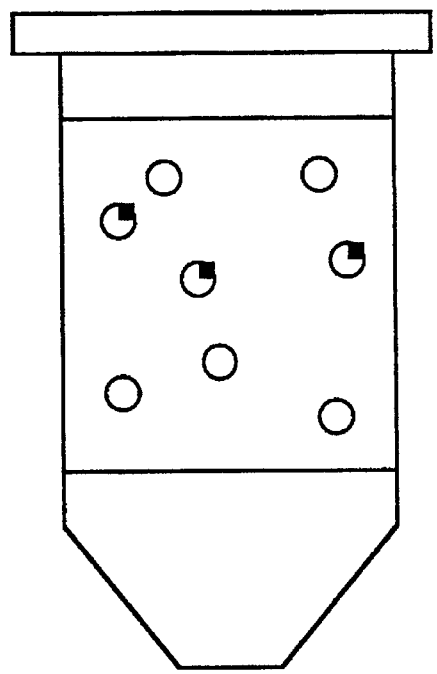
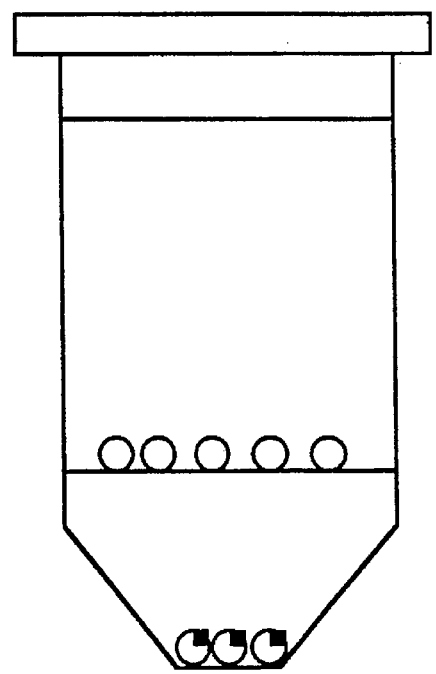
Fig. 11C        Fig. 11D

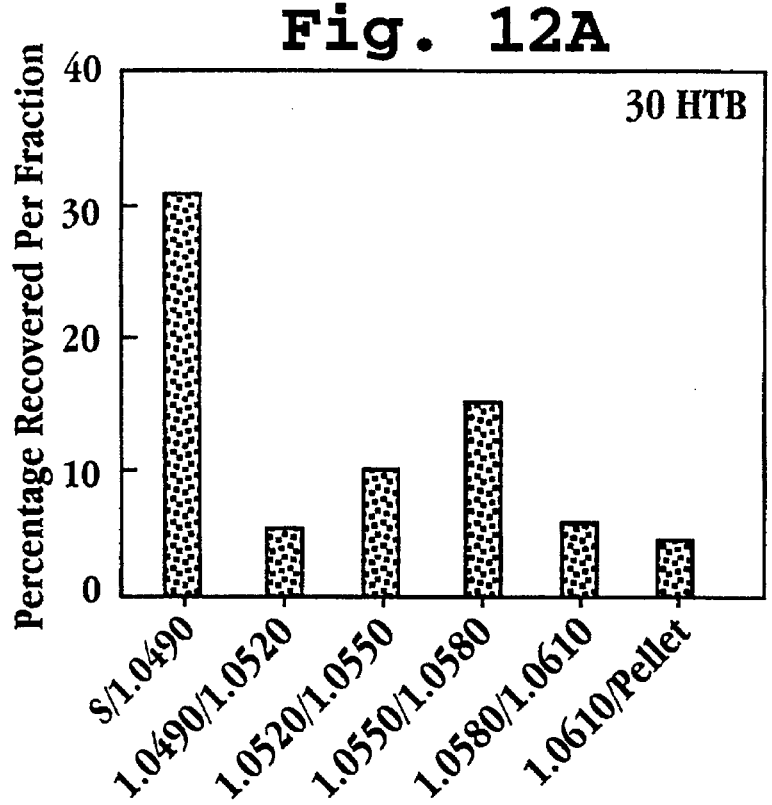
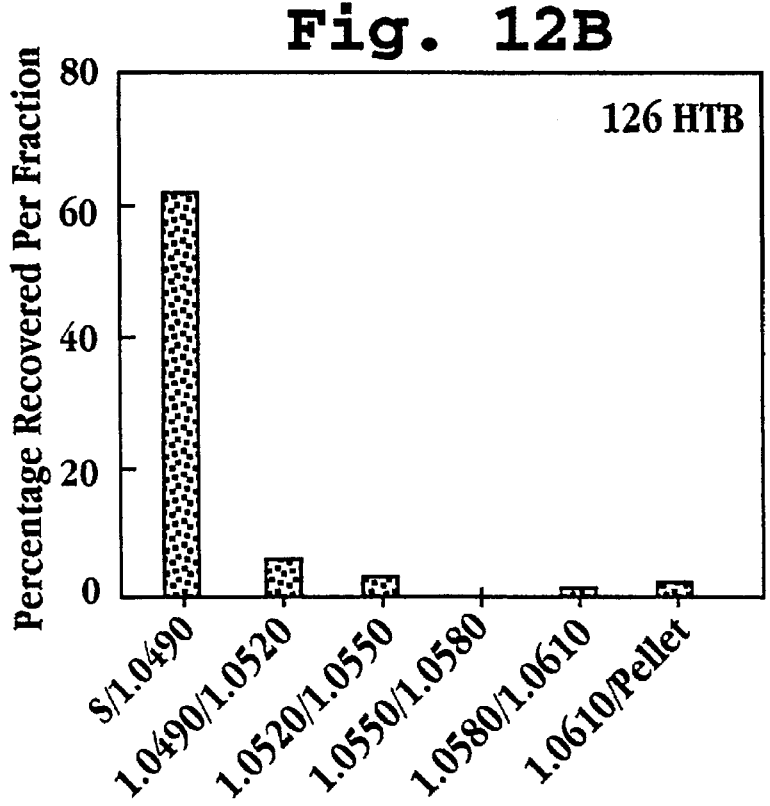

METHODS FOR ENRICHING BREAST TUMOR CELLS

1. INTRODUCTION

The present invention relates to methods of enriching breast tumor cells from a patient's body fluids. In particular, it relates to the use of a cell-trap centrifugation tube containing a specific density gradient solution adjusted to a specific density to enrich for breast tumor cells from a cell mixture. The tube allows the desired cell population to be collected by decantation after centrifugation to minimize cell loss and maximize efficiency. In addition, the method can be further simplified by density-adjusted cell sorting which uses cell type-specific binding agents such as antibodies and lectins linked to carrier particles to impart a different density to the non-tumor or tumor cell populations allowing the breast tumor cells to be separated from the non-tumor cells in a more convenient manner. The rapid breast tumor cell enrichment method described herein has a wide range of applications, including but not limited to, detection of tumor cells by molecular and immunochemical means, and purging of tumor cells from an autologous bone marrow cell preparation prior to re-infusion.

2. BACKGROUND OF THE INVENTION

Recent developments in anti tumor therapy include the use of autologous bone marrow or peripheral blood stem cell transplantation. Patients subjected to malignant cancers are often treated by lethal chemotherapy and radiotherapy followed by reinfusion of autologous peripheral blood or bone marrow collected prior to the lethal therapy. The decision to make autologous peripheral blood or bone marrow transplantation the treatment of choice for a given cancer depends upon the type of cancer itself and the degree of disease at the time of diagnosis. There is consensus that the autologous transplantation should be performed as soon as the disease is diagnosed and it is desirable to remove tumor cells, or other undesirable populations of cells, from the cells, tissues or fluids that are intended for autologous transplantation prior to infusion or implantation.

Diagnosis can be performed for tumors of the lympho-hematopoietic system by molecular means since a number of them are characterized by a genetic disorder that can be determined through use of specific primers and either fluorescent in situ hybridization (FISH) or polymerase chain reaction (PCR) followed by the use of specific probes. Solid tumors on the other hand may require detection at the cellular level using antibodies directed to tumor associated antigens or to tumor markers which occur in sites where the tumor cells are not normally not found (e.g. epithelial specific cytokeratins in the peripheral blood). In the latter case the detection is based on an immunohistochemical stain and a microscopic analysis of the cells. Both molecular and cellular detection mechanisms are dependent on the number of tumor cells in the cell sample. State of the art detection by PCR has sensitivity level of $1/10^5$ cells. This implies that by using specific primers, 1 cell in $10^5$ non-tumorous cells can be detected with cellular detection being $1/10^5$ to $1/10^6$ cells. In other words, contaminating solid tumor cells can be detected provided they represent between 0.001 and 0.0001% of the cell mixture. Given the limits of diagnostic detection of tumor cells, in addition to the low number of tumor cells that exist in circulating body fluids, current diagnostic procedures present a high probability of false negative diagnosis of solid tumors.

Among women, breast cancer is by far the leading cause of cancer, with invasive breast cancer affecting approximately one woman in nine. (Lippman, M. E., 1993, *Science* 259:631–632). The use of fine needle aspiration cytology or excisional biopsy under local anesthesia allows for outpatient diagnosis of breast cancer. Such diagnosis is usually performed in cases where a lump is found in the breast tissue either through routine physical examination, or by mammography, and/or where there is a family history of breast cancer (*Cecil Textbook of Medicine*, 19th ed., 1992, ed. Wyngaarden et al., pub. W. B. Saunders Co., pp.1381–1386). Since both fine needle aspiration and excisional biopsy procedures are invasive and expose the patient to a certain amount of risk, non-invasive approaches to the diagnosis of breast cancer are preferred.

It is established that breast tumor cells and tumor emboli spread directly to the bloodstream providing an alternative and desirable source of breast tumor cells for diagnostic purposes (Cecil Textbook of Medicine, supra). However, in order to successfully utilize circulating bodily fluids for breast cancer diagnosis, the small number of circulating breast tumor cells must first be enriched, and one must employ highly sensitive and specific techniques to detect the breast tumor cells.

At present, there is a need for a rapid and reproducible procedure suitable for processing a large volume of whole blood which produces high-yield, specific enrichment of breast tumor cells from circulating bodily fluids.

3. SUMMARY OF THE INVENTION

The present invention relates to methods of rapid and specific enrichment of breast tumor cells from circulating whole blood, bone marrow, lymph, and the like.

The invention is based, in part, on Applicant's discovery that colloidal silica (PERCOLL) solution adjusted to a density of 1.0490 to 1.0580 gr/ml, depending on the specific type of breast cancer, efficiently separates breast tumor cells from the majority of normal circulating cells in bodily fluids without prior separation if overlaid on the gradient solution. In addition, the method is improved by using cell-trap centrifugation tubes described herein which contain a constriction that allows the undesirable cells to be separated from the desirable cells.

The efficiency of the method is further improved when it is combined with the use of antibodies conjugated to heavy carrier particles in a manner by which the antibodies bind to antigens expressed by the undesirable cells, causing them to have a heavier density so that they are pelleted during centrifugation. The cells from the interface can then be collected and used directly for diagnostic purposes. Alternatively, the antibodies conjugated to carrier particles may be directed to antigens expressed by the desirable cells, and these cells can be recovered from the pellet. This method is hereinafter referred to as density adjusted cell sorting. In the case that the antibodies are directed to breast tumor cells, the cells from the interface are now depleted from tumor cells, and in the case of autologous transplantation, this technique provides an improved tumor-free graft.

A specific embodiment of the invention provides for a rapid and high yield single-step procedure to isolate breast tumor cells from a large volume of bodily fluid. The increased number of breast tumor cells in the resultant cell population enhances the sensitivity and accuracy of diagnosis.

The cell separation method described herein circumvents conventional methods which involve invasive procedures, i.e., fine needle aspiration or excisional biopsy under local anesthesia.

4. BRIEF DESCRIPTION OF THE DRAWINGS

FIGS. 5A–5F are cross-sectional views of alternative embodiments of the tube and constriction member of the invention.

FIGS. 6A and 6B are cross-sectional views of further alternative embodiments of the invention having multiple constriction members.

FIG. 7 is a cross-sectional view of a centrifuge syringe before the extraction of a specimen.

FIG. 8 is a cross-sectional view of the centrifuge syringe of FIG. 7 upon introduction of the specimen.

FIGS. 11A–11D illustrates the density adjusted cell sorting procedure.

FIGS. 12A–12D illustrate the enrichment of 4 breast tumor cell lines using the cell separation method of the present invention.

5. DETAILED DESCRIPTION OF THE INVENTION

Figure 1C:
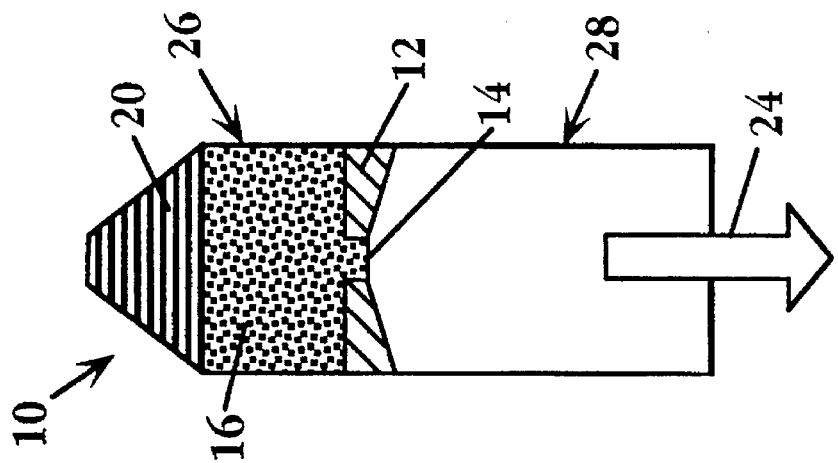
FIGS. 1A–1C are cross-sectional views of a preferred embodiment of the centrifugation tube according to the present invention, illustrating the steps of isolating or separating cells according to the invention.

The present invention relates to methods of rapid and high yield isolation or enrichment of breast tumor cell populations from cell sources or cell mixtures, based on density gradient centrifugation. More specifically, the present invention relates to the use of a specially designed cell-trap centrifugation tube containing a precisely determined density of a density gradient solution and a manner of collecting the desired cell population which maximizes yield. The method of the present invention may be used to increase the sensitivity of breast tumor detection by enriching the tumor cells from a cell source, e.g. whole blood, prior to the use of molecular or cellular detection techniques. In combination with tumor-specific antibodies and density adjusted cell sorting, this method allows the purging of tumor cells from a bone marrow or peripheral blood stem cell graft.

Breast tumor cells, like all other cells, have a particular density. The cell separation method of the present invention provides a method for enriching breast tumor cells from a given cell sample or cell mixture based on the density of the breast tumor cells, thereby increasing the tumor/cell ratio. Solid tumor cells have a morphology that is larger than average cells (e.g. neuroblastoma) or have the tendency to grow in clumps (e.g. breast tumor). This implies that these tumor cells have a lighter density than the rest of the sample. By providing a method which allows the separation of the majority of non-tumor cells while enriching the tumor cells, a better diagnosis should be possible.

5.1. BREAST TUMOR CELLS

The density of a given tumor cell is determined by centrifuging a tumor containing sample on a discontinuous density gradient ranging from 1.0490 to 1.0640 gr/ml. The majority of undesirable, non-tumor cells represent cells of the immune and hematopoietic system and have a density in the range of 1.0610 to 1.0770. The density of tumor cells generally falls within the 1.0490 to 1.0580 gr/ml density range. The density of the gradients is determined to an accuracy of within ±0.0005 gr/ml, preferably ±0.0002 gr/ml of the specific gravity of the desired cell. A method for determining the specific density of a given tumor cell is described infra.

Once a density range is determined where a given tumor cell is found, fine tuning of the density gradient can be performed and a single step enrichment can be performed. After centrifugation, the cells are collected and screened for the presence of tumor cells by morphologic, molecular or immunophenotypic means.

5.2. ENRICHMENT OF BREAST TUMOR CELLS BY DENSITY GRADIENT CENTRIFUGATION

The present invention relates to methods of rapid and high yield enrichment of breast tumor cells based on density gradient centrifugation. More specifically, the invention utilizes a precisely determined density of a density gradient solution contained within a specially designed cell-trap centrifugation tube to allow the breast tumor cells to be collected by decantation in order to maximize cell yield. These steps are taken, because the number of breast tumor cells in the starting cell mixture is usually very small, so that every effort directed to minimize cell loss during the cell separation process greatly enhances the accuracy of the subsequent use of the isolated cells.

A major advantage of the methods described herein is that a large volume of complete blood may be directly placed on the density gradient. Peripheral blood may be collected in anti-coagulant-containing tubes or by apheresis or leukopheresis. Complete blood does not need to be processed or diluted prior to centrifugation. However, since the methods enrich breast tumor cells based on their specific buoyant density, it is important that the cells are subject to separation within a relatively short time after their collection from an in vivo source because the density of the cells changes according to their culture or storage conditions. Therefore, in order to obtain optimal enrichment of breast tumor cells from blood, it is preferred that the blood samples are used within 48 hours after their collection. Most preferably, blood samples should be subjected to density gradient centrifugation within several hours of collection.

The present invention demonstrates that proper adjustments of a gradient material to a specific density, osmolality and pH greatly enhance cell separation. For the enrichment of breast tumor cells, a gradient should be adjusted to a density of 1.0490 to 1.0580±0.0005 gr/ml, depending upon the specific type of breast tumor cell, a physiologic osmolality of 270–290 mOsm/kg $H_2O$ and physiologic pH 6.8–7.8. In a specific embodiment by way of examples, breast tumor cells are directly loaded into a cell-trap centrifugation tube containing a "PERCOLL" solution filled to a level above the constriction, which has been adjusted to the specific density of between 1.0490 to 1.0580±0.0002 gr/ml, depending upon the specific type of breast tumor cell, osmolality of 280 mOsm/kg $H_2O$ and 7.4 pH. The density of the "PERCOLL" solution may be adjusted on a densitometer to precisely define its accuracy. It should be noted that a variety of other gradient materials may be used to achieve breast tumor cell enrichment, and they include, but are not limited to, "FICOLL", (a nonionic polymer of surcrose and epichlorohydrin) "FICOLL-HYPAQUE", (a mixture of 3,5-diacetamido-2,4,6-triiodobenzoic acid and a nonionic polymer consisting of sucrose and epichlorohydrin) cesium chloride, any protein solution such as albumin or any sugar solution such as sucrose and dextran. However, the density gradient solution should be prepared and adjusted to the appropriate density, osmolality and pH according to that disclosed herein, prior to their use. The gradient solution should be added to a centrifugation tube in a volume sufficient to allow all the cells having a higher density to pass through during centrifugation and to fit into the lower compartment of the tube. For example, a volume of about 20–25 ml of the solution is generally adequate for separating breast tumor cells in 20 ml of blood samples.

Any tubes suitable for use in centrifugation may be used for the practice of the invention. In particular, the present invention is directed to a cell-trap tube for the density separation of fetal cells. For the purpose of the present invention, a cell-trap tube refers to a centrifugation tube which contains within it a constriction or a trap and a properly adjusted density gradient material filled to a level above the constriction so that cells having a certain density pass through the opening of the constriction to form a cell pellet in the compartment below the constriction during centrifugation.

Figure 1B:
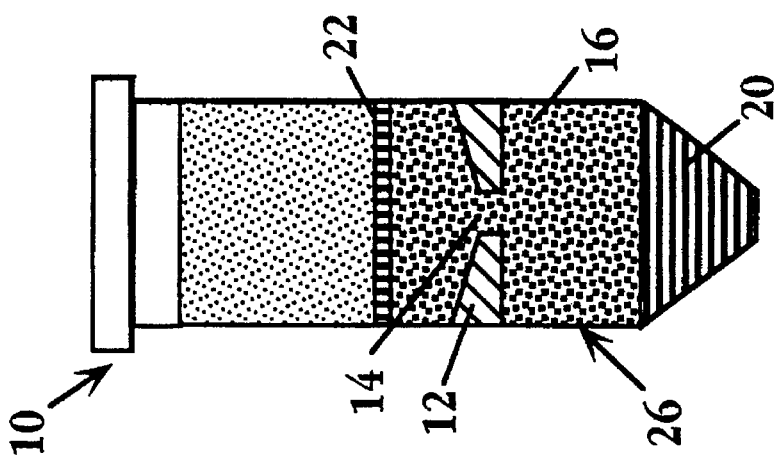
Figure 1A:
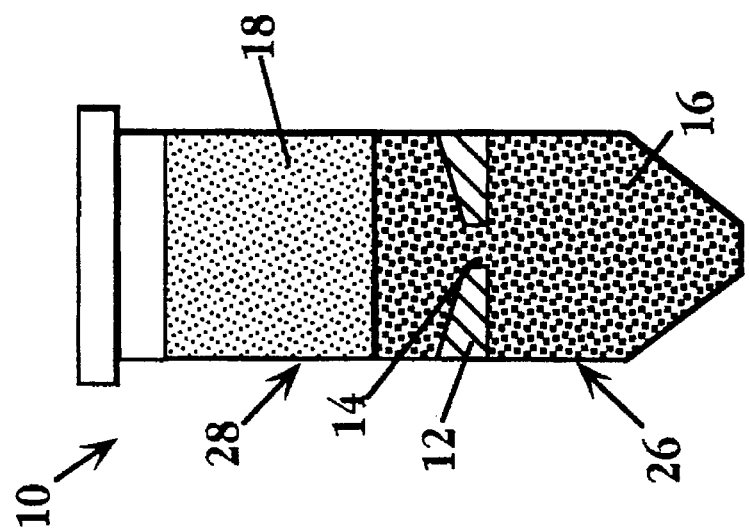
Figure 4A:
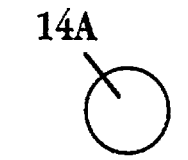
FIGS. 4A–4E illustrate examples of alterative shapes of the opening in the constriction member.
Figure 4B:
Figure 4C:
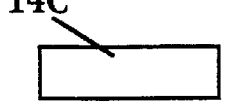
Figure 4D:
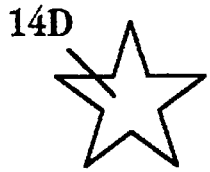
Figure 4E:
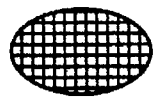

According to a preferred embodiment shown in FIGS. 1A and B, tube 10 includes constriction member 12, which defines central opening 14. The upper surface of constriction member 12 is preferably slightly angled inward, toward opening 14. The bottom surface of the constriction member also may be similarly, slightly angled (although not shown as such in the figures). In an exemplary embodiment, with a tube having an inner diameter of about 2.8 cm, the diameter of opening 14 formed by constriction member 12 is preferably about 0.5 cm. The size of opening 14 is generally not so small as to prevent heavier components of a sample, layered on top of the density gradient solution, from passing through the opening prior to actual centrifugation. Such a movement of components may occur due to normal gravitational forces. In general, the diameter of opening 14 is dictated by the ability to form an increased surface tension across the opening. A restriction that is little more than a rim around the interior of the barrel may be sufficient. Hence, the cross-sectional area of the aperture formed by the constriction member may be as little as about 5% or as great as about 95% of the horizontal cross-sectional surface area of the tube. In addition, the annular member may consist of a mesh or a sieve spanning the horizontal cross-section of the tube. In this case, the annular member is said to comprise a plurality of openings, such as illustrated in FIG. 4E.

Tube 10 is filled with density gradient solution 16 to a level above constriction member 12, or at least above opening 14. Preferably, with reference to a standard 50 ml centrifugation tube, density gradient solution 16 is filled to a level at least about 1 mm above the constriction member. The fluid sample to be separated is layered on the top of the density gradient solution, and the tube and its contents are subjected to centrifugation. Preferably, the sample is carefully layered so that at least about 1 mm of density gradient solution remains between the sample and the top of the constriction member after layering.

Referring to FIG. 1B, following centrifugation, components having densities greater than that of the gradient solution are found in a pellet 20 at the bottom of tube 10. Components having densities less than that of the density gradient solution remain floating at the top of the solution, in an interface 22 between the gradient solution and the remaining portion of the fluid sample solution. The interface portion is then poured off as indicated by arrow 24 in FIG. 1C. The provision of the density gradient solution to a level above the opening as described above helps to prevent the formation of an interface portion below constriction member 12.

Constriction member 12 facilitates pouring off the upper portion by providing a support or nucleus for formation of an intermediate surface tension across the surface of opening 14 when tilted for pouring. This surface tension impedes mixing of upper and lower portions of the tube when the contents of the upper portion are poured out of the tube. Constriction member 12 may be provided as an insert placed into a straight-walled tube. Alternatively, constriction member 12 may be formed as constriction of the tube wall during a molding process in the making of the tube itself. When the constriction member is provided by an insert, the insert may be movable to enable the operator to change the relative volumes of the lower portion 26 and upper portion 28 of tube 10 according to experimental conditions. The position of the constriction member in a molded tube can also be varied, during the manufacturing process, to provide tubes of differing relative upper and lower portion volumes. For example, in the isolation of cells from peripheral blood, a 20 ml sample of blood requires lower portion 26 to be about 15 ml in order to accommodate the relatively large amount of red blood cells that migrate to the pellet during centrifugation. By comparison, a 20 ml sample of apheresis or buffy-coat blood would require only about 10 ml in the lower portion.

In many applications, it will be desirable to collect only the supernatant fraction containing the interface portion. In such cases, the pellet is discarded with the tube. In other cases, the pellet can be removed by mechanical manipulation/disruption. For example, the tube can be inverted and subjected to vortex mixing. Such mixing will disrupt the pellet into the adjacent liquid phase and will induce movement of this liquid phase and disrupted cells from the lower or collection portion of the tube into the upper portion of the tube.

An advantage of the present invention is that the low density material above the constriction member is separated from material beneath by the simple act of pouring. This contrasts with many conventional methods of unloading gradient separations using standard straight-wall centrifuge tubes, where materials are separated by carefully pipetting out of the tube or, alternatively, by puncturing the bottom of the tube and allowing the contents of the tube to slowly drip out into collection vessels. Thus, the present invention provides a convenient, simple means for unloading differentially separated materials. In addition, unlike conventional straight-wall tubes, if the centrifuge tube of present invention is dropped or accidentally inverted, the contents will not readily mix due to the presence of the constriction member. Moreover, once separation has taken place, the solution present above the constriction member can be mixed in the tube, without disturbing (or fear of contamination by) the contents of the tube below the constriction member.

Figure 2A:
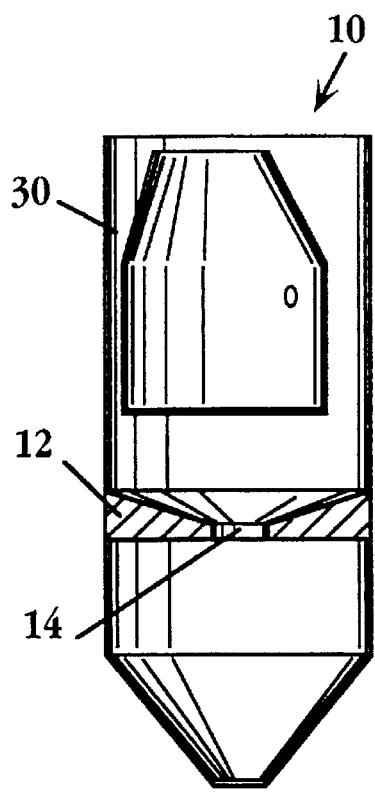
FIG. 2A is a schematic cross-sectional view of an alternative preferred embodiment of the present invention.
Figure 2B:
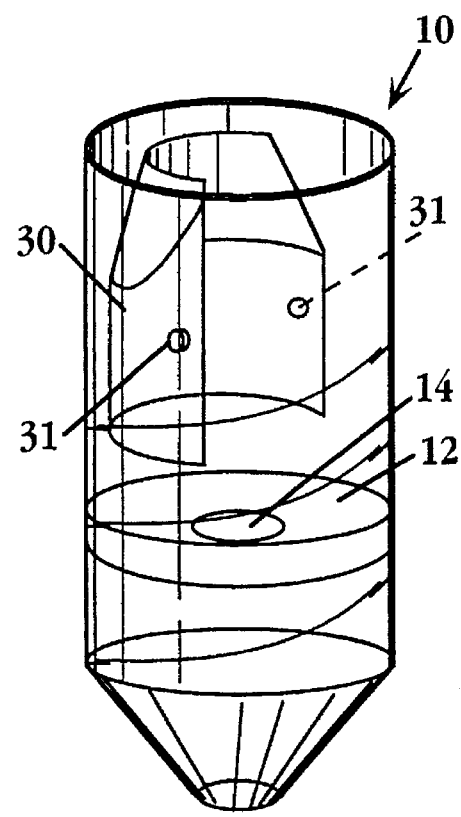
FIG. 2B is a perspective view of the embodiment of FIG. 2.

In an alternative preferred embodiment, tube 10 may be provided with insert or shield 30, as shown in FIGS. 2A and 2B. Shield 30 is provided above constriction member 12 to facilitate layering of the sample onto the gradient solution. Shield 30 may take the form of a roughly concentric insert placed in the upper portion of the tube and extending at least partially around the tube. In use, the operator pipettes material between shield 30 and the tube wall. The shield directs the material along the side of the tube to the top of the density gradient solution, while minimizing disturbance of the solution. As shown in FIG. 2B, tube 10 is a clear plastic or glass, with constriction member 12 formed as a separate insert. Shield 30 can be held in the upper portion of the tube, for example, by interference fit with spacers 31 biasing against the tube wall. Alternatively, shield 30 could be formed as a part of the tube.

Figure 3:
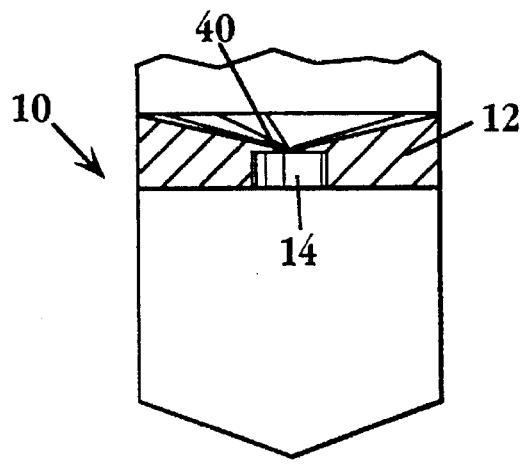
FIG. 3 is a cross-sectional view of an alternative embodiment of the constriction member of the invention with a valve.

The separation of materials may be further enhanced by the addition of valve 40 to the constriction member, as shown in FIG. 3. The valve 40 is located across opening 14. Valve 40 may be a one-way valve, or a valve that only opens upon application of a threshold centrifugal force. The valve can be formed by providing flaps of a softer material over the opening. In a preferred embodiment, the force required to open valve 40 would be about 850 times the normal force of gravity. Valve 40 thus allows heavy cells to pass through during initial centrifugation, and then keeps those cells in place, allowing for further processing of the lighter cells of interest located above the valve (such as washing or mixing of the cells). In this way complete and final manipulation of the cells can be performed in a single sterile container.

The shape of opening 14 is not limited to a circular shape, though in general, a funnel-shaped restriction forming a roughly circular shape 14A will be preferred. As shown in FIGS. 4A–D, the opening may also be oval 14B, rectangular 14C, star-shaped 14D, or any other shape that would create a restriction. Additionally, opening 14 may be covered by a mesh or grid, as illustrated in FIG. 4E.

FIGS. 5A–F are illustrations of alternative shapes and designs for the tube and constriction member according to the invention. FIG. 5A shows alternative tube 42 having a separate bottom compartment 44 for receiving the pellet to provide optimal collection of cells. Constriction member 12 is as previously described; it is funnel shaped on its upper surface and formed from a separate insert of plastic or, preferably, silicone. FIG. 5B shows a tube 46 with a pointed bottom wall. Tube 46 with the pointed bottom wall also enhances cell collection by allowing the heavier cells to form a better pellet, which may be desired if the cells are to be collected. Constriction member 48 is again an insert, but with a flat upper surface and wider opening. FIG. 5C illustrates alternative tube 50 with an integrally molded constriction member 52. FIG. 5D shows an alternative constriction member 54 that facilitate movement within tube 55 to adjust the relative volumes of the upper and lower portions. For this reason constriction member 54 has annular extending contact points 56. The constriction member will only contact the tube at these points, which create a fluid tight seal, but allow for easier adjustability. Tube 55 also has a flat bottom. FIG. 5E illustrates a further alternative embodiment of the present invention, wherein tube 60 includes cell trapping material 62, such as a sponge or gel. Material 62 may contain compounds that specifically bind certain cell types or toxins that kill specific cell types. Material 62 also may be made of a magnetic material if desired. Tube 64, shown in FIG. 5F, illustrates a further example of an integrally formed constriction member 66 in a tube with a flat bottom wall 68. Construction member 66 is located such that lower portion 26 has a smaller relative volume.

FIGS. 6A and B illustrate further alternative embodiments of the tube according to the invention. In each, two constriction members are provided. Second constriction member 12A is located above first constriction member 12B to create more compartments to allow separation of cells of differing densities. In FIG. 6A, the constriction members are shown as separate inserts, whereas they are integrally formed with the tube in FIG. 6B. Additional constriction members could also be added if a sample of several different densities is to be separated.

It will be applied by persons of ordinary skill in the art that the embodiments of FIGS. 2–6 are illustrated herein without density gradient solution for the sake of clarity only. Preferably, each embodiment would contain density gradient solution as described herein in connection with the embodiment of FIG. 1A.

In a preferred embodiment for therapeutic use, the cell-trap tube may be used in the form of a centifuge syringe, which is a completely enclosed system to ensure sterility.

One embodiment of centrifuge syringe 110 according to the invention is illustrated in FIG. 7. The centrifuge syringe 110 includes a specimen container 114 with a central orifice surrounded by fitting 112 adapted for receiving a needle 113, a handle 116 and a plunger 118. Fitting 112 may be any type of locking tip adapted to hold a needle, for example, a LuerLock™ syringe tip. Alternatively, fitting 112 may be a sterile septum adapted for connection with sterile fluid bags and tubes, for example a SAFSITE™ small wire extension set with reflux valve and Spin-Lock™ adaptor available from Burron Medical Inc., Bethlehem, Pa.

Handle 116 further preferably comprises knob 122 and a removable connection 124 to plunger 118. As shown in FIGS. 7–10, plunger 118 is single piece, machined or molded from a plastic material. Known medical grade plastic materials may be used. The plunger preferably has a funnel-shaped bottom wall 126 that is removably connected to the handle at connection 124. Side wall 127 preferably closely matches the container wall to permit sliding movement but provide an essentially fluid-tight barrier therearound. A top wall is formed by constriction member 128, which defines central opening 129. Alternatively, the outer diameter of side wall 127 may be slightly undersized to facilitate sliding and an o-ring seal provided between side wall 127 and container 114. Removable connection 124 may take the form of, for example, a screw fitting or a snap-fit. Preferably, connection 124 also provides for reattachment of handle 116. If reattachment is not desired, connector 124 may be designed such that handle 116 can be broken off. A suitable connection can be selected by those of ordinary skill in the art.

The plunger 118 is filled with a density gradient material 120 before the introduction of a specimen. Preferably, the density gradient material is filled to a level above the constriction member, or at least above the top of opening 129. For example, when using a standard 50 ml syringe, having an inner diameter of about 2.8 cm, the gradient material is preferably filled to a level about 1 mm or more above constriction member 128. This fill level will help to prevent the formation of an interface portion, as explained below, under constriction member 128.

Referring to FIG. 8, the introduction of the specimen into centrifuge syringe 110 is illustrated. Specimen 130 is drawn into the syringe through needle 113 secured to fitting 112, aided by the vacuum created by handle 116 and plunger 118 as the handle is pulled out of container 114, drawing the plunger away from fitting 112. The handle should be pulled with sufficiently low force and velocity to avoid mixing of the specimen with the density gradient material onto which the sample is layered. Preferably, when the handle is pulled density gradient may be prepared based upon the results of the second discontinuous density gradient. For example, if the material of interest is at the interface between densities 1.0700 and 1.0710, this implies that the particulate materials is denser than 1.0700 but lighter than 1.0710. To determine the final working density, the third discontinuous density range may be prepared with density gradient layers having a 0.0005 interval range with intervals being 1.0700, 1.0705, and 1.0710. The fourth digit in this case is accurate to within ±0.0002 which is the limit of detection of the Anton Paar apparatus.

A continuous self-generating density gradient may be prepared using "PERCOLL" which has the characteristic of forming a continuous gradient upon centrifugation at 30,000 g for 15 minutes. Under this condition, the silica particles of different size, forming the stock "PERCOLL", organize such that density changes occur at a microscopic level. A determination of the density range of a particulate material may be performed by layering the material on a pre-formed "PERCOLL" gradient. After the centrifugation, the particulate material may be collected from the gradient and its nature defined as described. The "PERCOLL" stock solution's characteristics can be defined as well. Because it is technically difficult to pull out an individual cell layer without contaminating it with layers above and below, it is preferred to combine the continuous density gradient technique with a series of discontinuous density gradients as described, infra.

Centrifugation in vertical rotors will form gradients of "PERCOLL" rapidly. Care must be taken to ensure that the compacted pellet of "PERCOLL" which may be formed under high speed centrifugation conditions does not contaminate the gradient during collection of the particulate matter of interest. It is not possible to use swing-out type rotors for self-generation of gradients due to the long path length and unequal g-force along the tubes. Zonal rotors can be used to form gradients of "PERCOLL" in situ, the gradients so formed will have the same characteristics as those generated in angle-head rotors. For self-generating gradients, centrifugation should take place at 30,000 $g_{av}$ for 15 minutes. The above-described procedure for determining density may be used to precisely define the specific density of any cell population of interest.

FIGS. 11(A–D) demonstrate the use of density adjusted cell sorting (FIGS. 11C and 11D) as compared to conventional density gradient centrifugation (FIGS. 11A and 11B). While the conventional methods are able to concentrate many irrelevant cell types to form a pellet, there are still a large number of undesired cell types trapped at the interface with the cells of interest (open circles, FIG. 11B). However, density adjusted cell sorting provides for the use of cell type-specific binding agents conjugated to heavy carrier particles with specificity for antigens expressed by the undesired cell populations, and incubating such agents with the cell mixture prior to centrifugation, so that such density-adjusted cells would be pelleted during centrifugation. Thus, although these cells are normally lighter than the gradient density, a heavier density is imparted to them due to the higher density of the carrier particles which are rendered cell type-specific by the antibodies used. When density adjusted cell sorting is applied to a cell mixture which is overlaid onto a customized density gradient contained within a cell-trap centrifugation tube, a single centrifugation step allows for substantial enrichment of a cell type of interest from any cell mixture.

For example, complete blood could be directly incubated with carrier particle- coated-anti-CD45 antibodies which react with most leukocytes. Since breast tumor cells do not react with anti-CD45 to any significant degree, the vast majority of the non-red blood cells, leukocytes, and other cells are rendered heavier than the density material and pellet during centrifugation, while the breast tumor cells remain in the upper compartment. A variety of such cell type-specific binding agents may be used to target specific cell types in the blood. These agents encompass antibodies such as the leukocyte-specific antibodies, e.g. anti-CD3, anti-CD4, anti-CD5 and anti-CD8 specific for T cells; anti-CD12, anti-CD19 and anti-CD20 specific for B cells; anti-CD14 specific for monocytes; anti-CD16 and anti-CD56 specific for natural killer cells; and anti-CD41 for platelets.

A positive selection procedure may be used to cause the breast tumor cells to be heavier than their normal density so that they are pelleted during centrifugation. Cell type-specific binding agents useful in the positive selection procedure include, but are not limited to antibodies to breast tumor antigens and antibodies to breast tumor markers, e.g. CA 15-3 (Kufe et al., 1984), CA 549 (Bray et al., 1987), cathepsin D (Westley et al., 1980), EGF-R (Osborne et al., 1980), estrogen receptor (Gorski et al., 1966), Ki-67 (Gerdes et al., 1983), progesterone receptor (Horowitz et al., 1983), and TGF-α, associated with breast cancer. Many of these antibodies are commercially available. In addition, cell type-specific binding agents include lectins such as wheat germ agglutinin and soy bean agglutinin, growth factors and cytokines. Furthermore, antibodies directed to any cell surface marker may be directly linked to heavy particles for use in density adjusted cell sorting, following conjugation methods well known in the art. It is noteworthy that when density adjusted cell sorting is applied, the specific density of the gradient is less critical, as long as the undesired cells are all rendered heavier. Although the methods of the present invention do not provide for the isolation of breast tumor cells to absolute purity, they allow the cells to be enriched substantially so as to enhance their use in subsequent prenatal diagnosis.

A number of commercially available carrier particles may be used in the present invention and include, for example, organic polymers, e.g. polyethylene; polypropylene; polyvinyl compounds e.g. polyvinylchloride, polyacrylonitrile, polyacrylate, polymethacrylate, polycarbonate and copolymers thereof; polystyrene latex; nylon; polyterephthlate; and the like, or inorganic polymers, e.g. glass or silica particles; cellulose, polysaccharides, e.g. agarose, cellulose, Sepharose, Sephadex, etc., or combinations thereof. The carrier particles may be from naturally occurring polymers, modified naturally occurring polymers and synthetic addition and condensation polymers. A preferred carrier particle of the present invention is a silica particle between 0.1–5.0 microns coupled to an aminopropyl group and having a density of greater than 1.08 gr/ml. U.S. Pat. Nos. 4,927,750 and 4,927,749, issued May 22, 1990, describe examples of modified silanes which may be used in the present invention as carrier particles. Various carrier particles are commercially available from, for example, Bangs Laboratories, Inc., Carmel, Ind., Pharmacia, Sigma Chemical Company, Bio-Rad, AMAC, Inc., etc. A preferred heavy carrier particle of the present invention is one having a density greater than 1.08 gr/ml and a particle size of 0.1 micron to 5.0 micron such that the carrier particles will be pelleted upon centrifugation, as well as one having the capability of binding, either directly or indirectly to cell-type specific binding agents.

Immobilization of a cell-type specific binding agent to carrier particles can be achieved by a variety of techniques at an appropriate force, the sample will form a stream which adheres to the side of the container as it is drawn in, as shown in FIG. 8. This will reduce unwanted mixing. Mixing of the two materials is also minimized by the fact that the density of the specimen is significantly lower than the density of the density gradient material. After specimen 130 is drawn into container 114, the container is maintained in an upright position and the sample lies on top of density gradient material 120.

Using needle 113, a sample such as peripheral blood may be drawn directly from a patient for analysis. The present invention thus ensures sterility of such a sample by completely eliminating direct handling of the sample prior to introduction into the centrifugation container. Alternatively, using a sterile septum, blood previously collected by known techniques and stored, for example in a sterile bag, may be drawn into the centrifugation container through sterile tubing or other known sterile connection means. The present invention thus ensures a sterile transfer of sample material on a larger scale in a completely closed system, again without direct handling of sample material.

Once the specimen has been completely drawn into the container 114, and the handle 116 has been pulled so that the removable connection 124 is located at the central orifice of the specimen container 114, the handle 116 can be removed for the centrifugation step.

Figure 9:
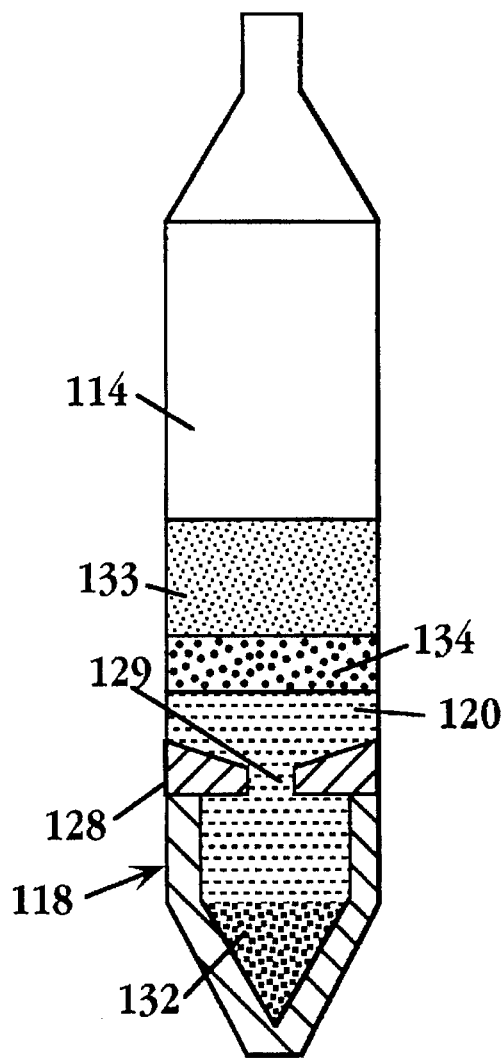
FIG. 9 is a cross-sectional view of the centrifuge syringe of FIG. 7 after centrifugation.

FIG. 9 illustrates the centrifugation syringe after the centrifugation step has been performed. As shown, the handle 116 has been detached from the plunger 118, which is located at the bottom end of the container 114. Centrifugation of container 114 results in a pellet 132 being formed from the heavier portions of the specimen at the bottom of the plunger 118. Density gradient material 120 is located above pellet 132. An interface portion 134, which contains the cells of interest, is formed between specimen diluent 133 and density gradient material 120, and above constriction member 128.

Figure 10:
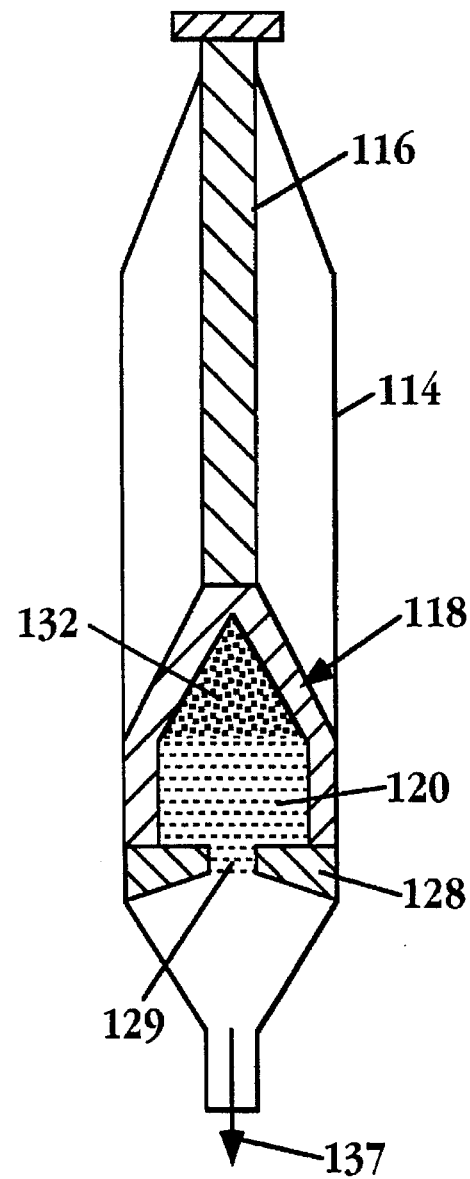
FIG. 10 is a cross-sectional view of the centrifuge syringe of FIG. 7 upon removal of the specimen.
Figure 12C:
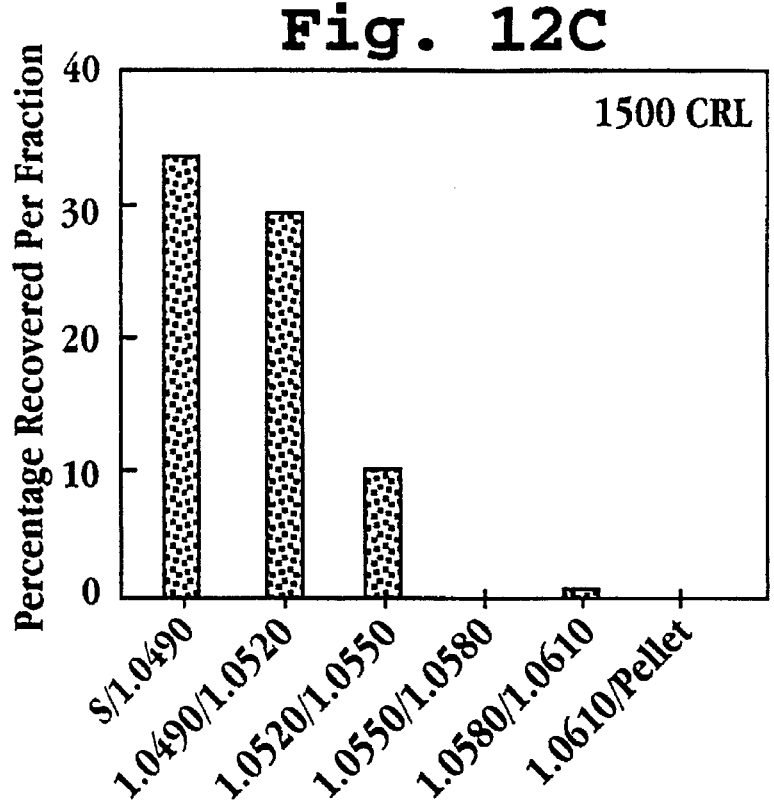
Figure 12D:
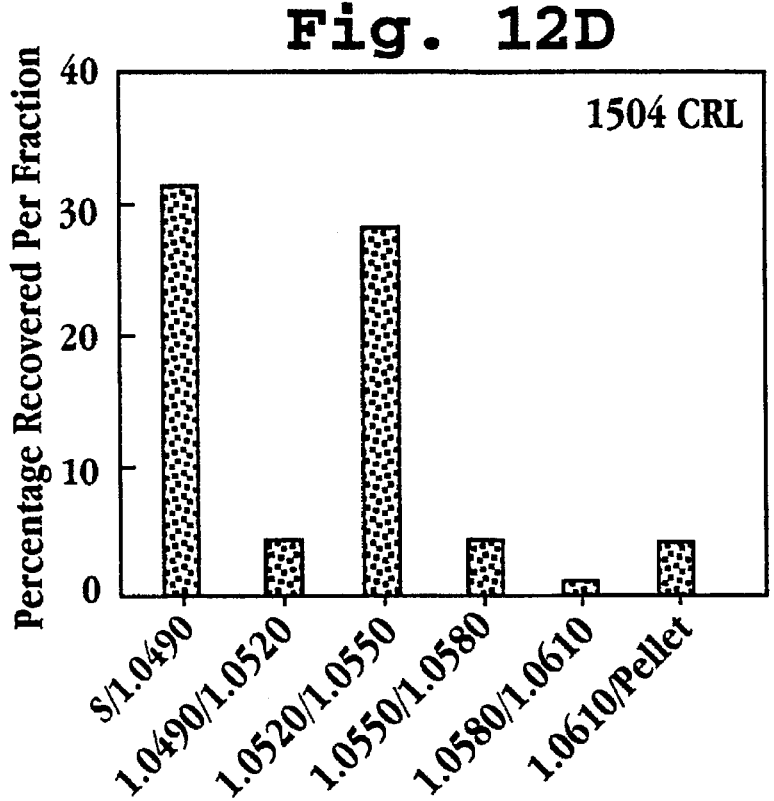
Figure 13A:
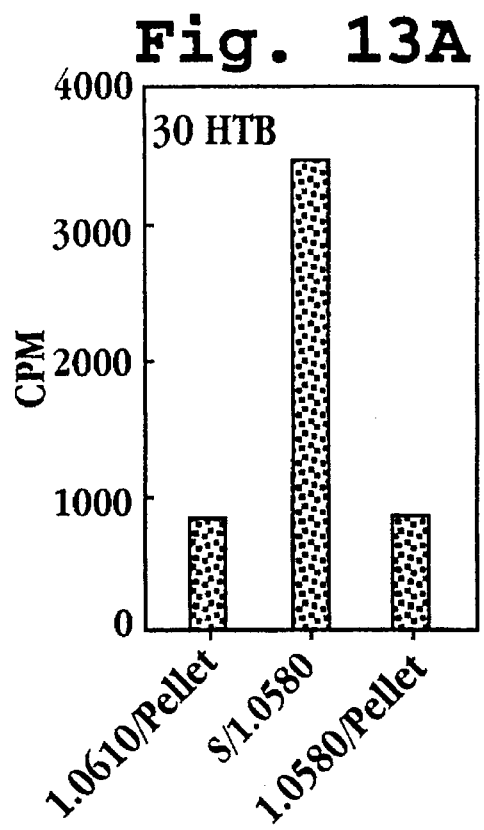
FIGS. 13A–13D illustrate that the ideal density for enrichment of breast tumor cells spiked in a cell mixture is 1.0580.
Figure 13B:
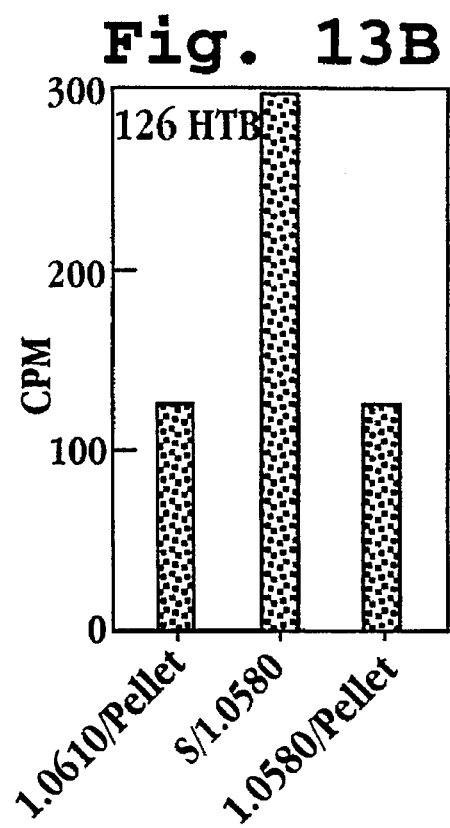
Figure 13C:
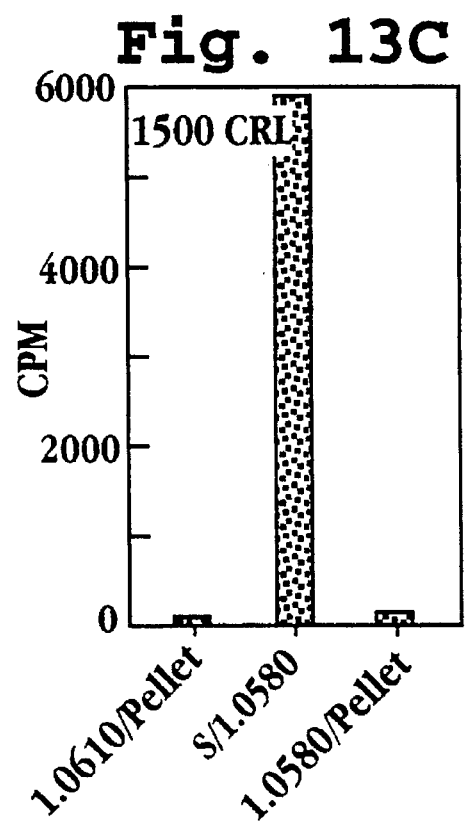
Figure 13D:
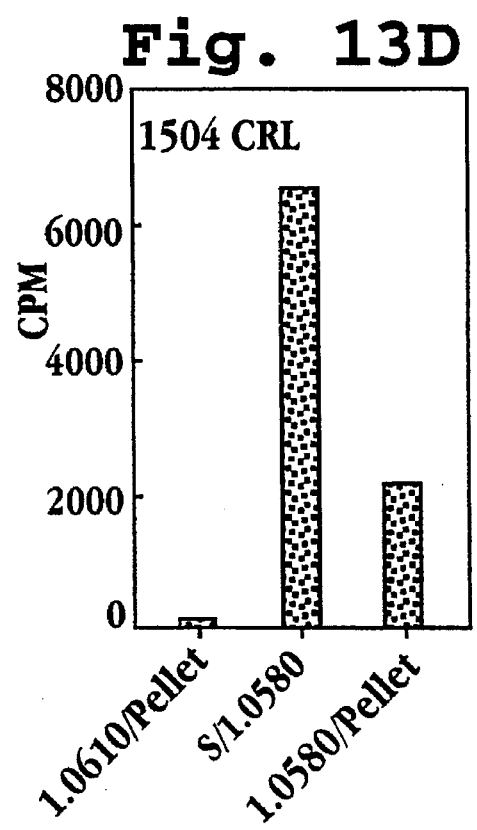

Interface portion 134 may be removed from the centrifuge syringe 110 by inverting the centrifuge syringe and ejecting it off as indicated by arrow 137 in FIG. 10. Further removal of density gradient material 120 and the pellet 132 can be facilitated by reattaching handle 116 to plunger 118 at connection 124. The handle then can be pushed into the container to aid the removal of the material if necessary.

5.3. DENSITY ADJUSTED CELL SORTING

Density gradient centrifugation is a method of separating cells based on the different densities of cell types in a mixture. The method is often used in a single step to separate cells into two compartments which contain cells that are either lighter or heavier than a specific density of the gradient material used. However, due to the imprecision of the procedure, the use of a single density usually does not allow the cells of interest to be enriched to a significant level of purity, especially if the cells are present in a low number among many undesired cell populations. Thus, density gradient centrifugation is most often carried out through repetitive steps based on a series of different density gradients or in combination with affinity chromatography, cell panning, cell sorting, and the like. Alternatively, discontinuous density gradient centrifugation may be performed using multiple layers of the different gradient densities. This method allows cells of different densities to form zones or bands at their corresponding densities after centrifugation. The cells in the different zones are then collected by placing a pipette at the appropriate location. Such a method is difficult to carry out in a routine manner in a clinical setting because it requires skilled personnel for the preparation of the gradient, and there is often mixing between the different layers of the density solution before and/or after centrifugation that potentially disrupts cell separation. Most importantly, the above-described procedures require multiple steps that unavoidably cause substantial cell loss, thus they are not amenable for the separation of cells present in a low number within a mixture in a routine manner.

The present invention circumvents these problems by combining density gradient centrifugation and affinity cell separation into a single method referred to as density adjusted cell sorting. This method modifies the conventional positive and negative selection by solid phase binding methods, and combines it with a specific density gradient selected from the range of 1.0490±0.0002 to 1.0580±0.0002 gr/ml for breast tumor cell separation. The methods of cell separation of the present invention require the determination of the density of the desired cell type with an accuracy of ±0.0005 gr/ml, preferably ±0.0002 gr/ml. The density of a given unknown particulate material, may be determined using a series of discontinuous density gradients, each discontinuous density gradient step depending on the exactness of the previous one, or using a continuous density gradient in addition to a discontinuous gradient.

For a discontinuous gradient, a "PERCOLL" stock solution may be prepared as defined infra for the appropriate application. The density of the stock solution up to the fourth digit may be determined using appropriate equipment, for example, an Anton Paar apparatus which measures density with an accuracy of ±0.0002 gr/ml. The osmolality of the stock solution may be adjusted appropriately, for example, to 280 mOsm/kg $H_2O$±10 for human use or 320 mOsm/kg $H_2O$±10 for animal use. The pH may be adjusted appropriately, preferentially to 7.4 if a physiologically isotonic solution is desired. The stock "PERCOLL" may be diluted with diluent having the appropriate pH and osmolality and the density may be defined at any time during the procedure using appropriate instrumentation.

For preparation of the first discontinuous density gradient, the following densities of stock "PERCOLL" may be prepared: 1.1250, 1.1150, 1.1050, 1.0950, 1.0850, 1.0750, 1.0650, 1.0550, 1.0450, 1.0350, 1.0250, 1.0150, and 1.0050. The densities should all be accurate to within the range of ±0.0002 gr/ml at 280±10 mOsm. The different densities of "PERCOLL" are layered carefully on top of each other using a pipette or a syringe fitted with a wide-bore needle, the heaviest on the bottom and the lightest on the top. The desired particulate matter whose density is to be determined may be layered on the top of the discontinuous density gradient taking care not to mix the particulate material on top of the discontinuous density gradient. The density gradient is centrifuged for 30 minutes at 850 g at room temperature. The particulate material is collected from the different interfaces and defined by its nature, i.e., morphology, molecular, and biochemical standards or immunophenotypic means. This first discontinuous density gradient allows determination of the density range of the particulate material. For example, if the particulate material is at the interface between 1.0750 and 1.0650, the particulate material is denser than 1.0650 and lighter than 1.0750. A second set of density gradients is prepared with a 0.0010 intervals, for example: 1.0650, 1.0660, 1.0670, 1.0680, 1.0690, 1.0700, 1.0710, 1.0720, 1.0730, 1.0740, and 1.0750, etc. and the process of preparing the gradients performed as described and the centrifugation repeated. The particulate material may be collected from the different interfaces and defined by its nature as described. A third discontinuous known to those skilled in the art. Such techniques are described in, for example Bangs (*The Latex Course* (1992), available from Bangs Laboratories, Inc. Carmel, Ind.) Yoshioka et al. (*Journal of Chromatography* 566:361–368 (1991)); Pope et al. (*Bioconjugate Chem.* 4:166–171(1993)); Harlow and Lane 1988 (*Antibodies: A Laboratory Manual*, Colorado Spring Harbor Laboratory); *Avtdin-Biotin Chemistry: A Handbook* (1992), ed. Savage et al., pub. PIERCE; Hermanson et al., *Immobilized Affinity Ligand Techniques* (1992) pub. Academic Press, Inc. Binding techniques include, for example, simple physical absorption or adsorption where the cell-type specific binding agent is bound directly to the carrier protein without the use of functional groups; complex adsorption where a second binding agent, e.g. BSA, is co-adsorbed to the carrier particle and forms the basis for binding functional groups; and covalent bonding of the binding agent to the carrier particle. The biotin-strepavidin affinity system may also be used in the present invention to bind cell-type specific binding agents to the carrier particles. Various particle surface chemical reactions for covalent coupling are known to those of skill in the art and include, but not limited to, carboxylic acid, primary or aliphatic amine, aromatic amine or aniline, chloromethyl (vinyl benzyl chloride), amide, aldehyde, hydroxyl, thio, hydrazide, epoxy, sulfate and sulfonate. Other coupling chemical reactions are described in Bangs, Uniform Latex Particles (1984).

In the present invention, it is preferred that the direct or indirect binding of the cell-type specific binding agent to the carrier particle be performed in excess binding agent to allow for maximum coverage of the surface of the carrier particle, thereby reducing the potential for non-specific binding. Carrier particles may also be subjected to blocking agents, e.g. casein, gelatin and Tween to fill any unoccupied sites on the carrier particle in order to reduce non-specific binding.

In one illustrative example of a coupling reaction, carboxyl groups on the carrier particle surface can be made reactive with the available amino groups on the cell-type specific binding agent. Other means of binding cell-type specific binding agent to particle surfaces include employing activated carboxylic acids, carbodiimides, i.e., (1-ethyl-3-(3-dimethylaminopropyl) carbodiimide or EDAC, imido esters, active alkyl halides, etc., to form amido, amidine or amino linkages.

A preferred carrier particle of the present invention is an aminopropyl silica particle wherein the amino groups have been coupled to the silica particle through a glutaraldehyde linkage.

5.4. HIGH YIELD OF BREAST TUMOR CELLS FOR IMMUNOPHENOTYPIC TESTING

The cells enriched by the methods described in Section 6 may subsequently be examined for the presence of breast tumor cells. The resultant yield of isolated or enriched cells from the cell separation methods of the present invention may be used for diagnostic purposes, e.g. morphological, molecular, biochemical or immunophenotypic assays. For example, DNA may be prepared from the collected cells and subjected to polymerase chain reaction (PCR) or the collected cells may be assessed morphologically thereby avoiding the use of invasive and expensive surgical procedures heretofore relied upon for such a determination.

Various breast tumor antigens and breast tumor markers are known to those of skill in the art or are commercially available including but not limited to cathepsin D (Westley et al., 1980), EGF-R (Osborne et al., 1980), estrogen receptor (Gorski et al., 1966), Ki-67 (Gerdes et al., 1983), progesterone receptor (Horowitz et al., 1983), and TGF-$\alpha$, associated with breast cancer. Antibodies directed to these antigens or markers may be used to assess the tumor type of collected cells.

6. EXAMPLE

DETERMINATION OF DENSITY OF BREAST TUMOR CELL DENSITY AND THEIR ENRICHMENT BY DENSITY GRADIENT CENTRIFUGATION

6.1 MATERIALS AND METHODS

Cells were incubated with $^3$H thymidine for 24 hours under standard culture conditions according to methods known in the art. The cells were mixed with buffy coat from peripheral blood.

6.1.1. PREPARATION OF DENSITY GRADIENTS

"PERCOLL" solution was purchased from Pharmacia Biotech (Upsala, Sweden) and stored at 4° C. according to the recommendation of the vendor. A stock solution was prepared by mixing 12 parts of "PERCOLL" with 1 part of 10 × calcium and magnesium-free phosphate buffered saline (PBS). The pH of the solution was adjusted to 7.4 and the osmolality to 280 mOsm/Kg $H_2O$. For use in enriching breast tumor cells obtained from in vitro cell lines in a cell mixture, the stock solution was further diluted with calcium and magnesium-free PBS into five different fractions with respective densities of 1.0490, 1.0520, 1.0550, 1.0580, and 1.0610 and used at room temperature. It was crucial to adjust the density of the gradient with an accuracy of ±0.0002 gr/ml point in order to ensure reproducibility and accuracy of cell separation. This was done by a high precision digital density meter such as DMA 48 (Anton PAAR U.S.A., Ashland, Va.). All procedures were performed under sterile conditions and at room temperature.

6.1.2. DENSITY GRADIENT CENTRIFUGATION

Radioactively labeled breast cancer cells were mixed with a buffy coat from a healthy donor and centrifuged on the discontinuous gradient. Cell mixtures containing the breast tumor cells from cell lines 30 HTB, 126 HTB, 1500 CRL and 1504 CRL were layered on a "PERCOLL" gradients previously adjusted to a densities in the range of 1.0490–1.0610, ±0.0002 gr/ml, an osmolality of 280 mOsm/Kg $H_2O$, and a pH of 7.4 in a 50 ml conical cell-trap tube. The tube contained a constriction in a location so that approximately 15 ml of "PERCOLL" was in the lower compartment and 5 ml of "PERCOLL" was above the constriction. It was critical to completely fill the volume under the constriction with "PERCOLL" to prevent the formation of air bubbles. Generally, 20 ml of cell samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet in the compartment below the constriction were prevented from pouring off when the tube was inverted. After centrifugation at 650×g for 10 minutes at room temperature, the fluid on top of the pellet was removed with a pipette, and the cells in the pellet resuspended in PBS. Since this low speed centrifugation step was primarily used to concentrate the cells of interest into a pellet, while removing cell debris and platelets in the fluid, a cell-trap could also be used to facilitate this step. In this alternative embodiment, a modified 50 ml cell-trap tube was used in which the constriction was placed near the bottom of the tube so that a small volume of about 0.5 ml was below it. This design protects the pellet and reduces cell loss during removal of the fluid above the pellet after centrifugation. This specific feature would allow the method of the invention to be automated without the need for cell sorting. Which was performed to reduce contaminating cells, particularly platelets.

6.2 RESULTS

The densities of four breast tumor lines were determined using "PERCOLL" discontinuous density gradient system (FIGS. 12A–12D). The cells were collected from each of the interfaces and counted in a hemocytometer. The results showed that 30 to 60% of the tumor cells have a density equal to or higher than 1.0580 g/ml (FIG. 13A–13D). This implies that the fraction containing tumor cells was between 10 and 80% pure. Of the cells collected in a specific density of 1.0580, approximately 75 to 85% of the total cells were tumor cells, while approximately 10% of the total cell volume was a contaminant. This implies that the detection limit of the assay is improved approximately 10 times from $1/10^6$ to $1/10^5$.

When radioactively labeled breast tumor cells were mixed with a peripheral blood buffy coat, up to 80% of them could be removed by centrifuging the mixture on a 1.0580 g/ml, 280 mOsm gradient. In addition, only a small fraction (<10% of initial cell number) of non-tumor cells contaminated the collected tumor fraction.

Applicants believe that the density ranges shown in FIGS. 12A–12D and 13A–13D, obtained from using cultured breast tumor cells, are applicable to breast tumor cells obtained from in vivo sources. It will be apparent to those of skill in the art that slight variations in the densities of various breast tumor cells from in vivo sources may necessitate refinement of the exact density necessary to achieve optimum enrichment. Methods for determining specific densities with an accuracy of ±0.0002 gr/ml are disclosed herein.

7. EXAMPLE

METHOD FOR BINDING ANTIBODY TO GLASS BEADS

7.1 PREPARATION OF THE BEADS

Silica beads (1.4 microns) obtained from Bangs Laboratories, Carmel, Ind. were washed with concentrated HCl for 2 hours at room temperature and vortexed intensely every 15 minutes to brake up bead clumps. After washing, the beads were centrifuged at 850 g for 5 minutes. The HCL containing supernatant was decanted and the beads were washed with deionized H₂O with intensive vortexing to brake up the clumps.

The beads were incubated at room temperature overnight in concentrated nitric acid with constant stirring using a magnetic stirrer. The beads were then centrifuged at 850 g for 5 minutes and washed 3 times with deionized water, using 50 ml of deionized H₂O at each step. The beads were vortexed intensely in between each wash to avoid bead clumping. To prevent microbacterial contamination, the beads were stored at 0–4 degrees centigrade in deionized H₂O until further use.

7.2 SILANIZATION OF THE BEADS

To silanize the beads, either 3-aminopropyltriethoxysilane, (3-iodopropyl) trimethoxysilane or [1–9trimethoxysilyl)-2(m-(or p) chloromethyl)phenyl] ethane were used. Forty mls of silane solution (a 10% solution in 95% ethanol/deionized H₂O) was added per 4 gr of beads. The bead mixture was rotated end over end for 1 hour at room temperature. The beads were centrifuged at 850 g for 5 minutes and the excess silane was washed off using 95% ethanol/deionized H₂O in a volume of 100 ml. The beads were vortexed intensely in between each wash step to avoid bead clumping. After the washing step, the beads can be dried and stored. Alternatively the beads can be stored in 95% ethanol/deionized H₂O in the cold which prevents clumping of the beads.

7.3 ANTIBODY COUPLING TO THE AMINOPROPYL GLASS

The silanized beads were incubated overnight in 2.5% glutaraldehyde at room temperature. The next day, the beads were centrifuged at 850 g for 5 minutes and the free glutaraldehyde was washed off with deionized H₂O in a volume of 100 ml per 5 gr beads. The beads were vortexed intensely in between each wash step to avoid bead clumping.

The antibody was added to the aminopropyl beads in an excess, at least 3 mg/m² total bead surface and rotated end over end overnight at room temperature. The next day, the beads were centrifuged at 850 g for 5 minutes and the free protein was washed off with 100 ml of deionized H₂O. The beads were vortexed intensely in between each wash step to avoid bead clumping. The beads were stored in deionized H₂O containing 0.1 sodium azide in the cold. The final bead suspension should contain 70–90% single beads and 10–30% predominantly duplet and triplet beads.

The binding efficiency of the antibody conjugated beads (in terms of the percent of beads that are coated) can be determined using flow cytometric analysis and a fluoresceinated antibody directed to the coupled antibody. Alternatively, the antibody may be added to the silanized beads directly without the glutaraldehyde linking.

Various modifications of the invention, in addition to those shown and described herein, will become apparent to those skilled in the art from the foregoing description. Such modifications are intended to fall within the scope of the appended claims.

All references cited herein are hereby incorporated by reference in their entirety.

What is claimed is:

1. A method of enriching breast tumor cells from a cell mixture, comprising:

layering a cell mixture containing the breast tumor cells onto a gradient density solution contained in a centrifuge tube;

said tube having a first closed end defining an inner bottom wall and an opposite open end, an annular member disposed in said tube and defining an opening therethrough, wherein said opening has an area less than the area of a cross section of said tube, said annular member defining a lower portion of the tube extending between said member and said tube bottom wall and an upper portion above said annular member said tube containing a density gradient solution which fills said lower portion and a part of said upper portion to a level above said annular member prior to centrifugation, of said tube;

said density gradient solution having an osmolality of 280±10 mOsm and a specific density within 0.0005 gr/ml of the specific density of said breast tumor cells;

centrifuging said tube at a gravitational force sufficient to pellet cells having specific densities greater than the specific density of the density gradient material in said tube; and collecting from the upper portion of said tube an enriched population of breast tumor cells.

2. The method of claim 1 wherein the specific density is within 0.0002 gr/ml of the specific density of said breast tumor cells.

3. The method of claim 2 wherein the specific density of the density material is selected from the range 1.0490–1.0580 g/ml.

4. The method of claim 3 wherein the specific density of the density material is 1.0580 g/ml.

5. The method of claim 1 wherein the breast tumor cells in the upper portion are collected by decantation.

6. The method of claim 1 further comprising incubating said cell mixture with a cell type-specific binding agent linked to carrier particles prior to centrifugation, said particles having a specific density that is at least 0.001 gr/ml greater than the specific density of said density gradient solution.

7. The method of claim 6 wherein the cell-type specific binding agent specifically binds to a cell selected from the group consisting of leukocytes, B-cells, monocytes, natural killer cells and platelets, and such binding agent does not bind to breast tumor cells.

8. The method of claim 7 wherein the agent is an antibody.

9. The method of claim 8 wherein the antibody is directed to CD45 antigen.

10. The method of claim 6 wherein the particles are glass beads.

11. The method of claim 6 wherein the beads are silane-activated.

12. The method of claim 11 wherein the silane is 3-amino propyltriethoxy silane.

13. The method of claim 1, wherein the density gradient solution is selected from the group consisting of "PERCOLL", "FICOLL", "FICOLL-HYPAQUE", albumin, sucrose, and dextran.

14. A centrifugation tube, comprising:
a tube adapted for centrifugation having a first closed end defining an inner bottom wall and an opposite open end;

an annular member disposed in said tube and defining an opening therethrough, wherein said opening has an area less than the area of a cross section of said tube, said annular member defining a lower portion of the tube extending between said member and the tube bottom wall and an upper portion above said annular member; and a density gradient solution having a density selected from the range 1.0490–1.0580±0.0002 gr/ml at 280 mOsm and filling said lower portion and a part of said upper portion of said tube to a level above said annular member.

15. The tube of claim 14, wherein said density gradient solution fills the upper portion to a level at least about 1 mm above said annular member.

16. The tube of claim 14, wherein said annular member is formed integrally with said tube.

17. The tube of claim 14, wherein said annular member is slidably disposed within said tube to permit adjustment of the volume of the lower portion.

18. The tube of claim 14, wherein said annular member defines a plurality of openings.

* * * * *